United States Patent
Mah

(10) Patent No.: US 9,788,917 B2
(45) Date of Patent: *Oct. 17, 2017

(54) METHODS AND SYSTEMS FOR EMPLOYING ARTIFICIAL INTELLIGENCE IN AUTOMATED ORTHODONTIC DIAGNOSIS AND TREATMENT PLANNING

(71) Applicant: ClearCorrect Holdings, Inc., Round Rock, TX (US)

(72) Inventor: James Mah, Las Vegas, NV (US)

(73) Assignee: ClearCorrect Holdings, Inc., Round Rock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/376,656

(22) Filed: Dec. 13, 2016

(65) Prior Publication Data

US 2017/0086943 A1    Mar. 30, 2017

Related U.S. Application Data

(63) Continuation-in-part of application No. 14/831,648, filed on Aug. 20, 2015, now Pat. No. 9,517,111.

(Continued)

(51) Int. Cl.
*G06F 15/18* (2006.01)
*A61C 7/00* (2006.01)
(Continued)

(52) U.S. Cl.
CPC .......... *A61C 7/002* (2013.01); *A61B 1/00009* (2013.01); *A61B 1/00011* (2013.01);
(Continued)

(58) Field of Classification Search
None
See application file for complete search history.

(56) References Cited

U.S. PATENT DOCUMENTS 6,616,444 B2 *  9/2003  Andreiko et al. ................ 433/3
7,991,485 B2 *  8/2011  Zakim ............................. 700/2
(Continued)

OTHER PUBLICATIONS

Zarei et al., "A Novel Neuro-Fuzzy Assessment Index for Orthodontics", Jun. 19, 2009, Proceedings of International Joint Conference on Neural Networks, pp. 3493-3497.*

(Continued)

*Primary Examiner* — Paulinho E Smith
(74) *Attorney, Agent, or Firm* — Locke Lord LLP

(57) ABSTRACT

A method for treating an orthodontic condition can include receiving patient data, such as through a website, accessing a database having information derived from patient treatments, generating a model of an orthodontic condition defining one or more anatomic features of a set of teeth, identifying a diagnosis of an orthodontic condition and identifying a treatment regimen for the diagnosis. A method can include tagging an anatomic feature with an electronic identifier and automatically generating a tooth setup. A system can include a server and a database, which can include information relating to patient treatments, and a website for receiving patient data. A system can include an electronic model representing anatomic features of a patient's teeth and an application adapted to identify a diagnosis and a treatment regimen for an orthodontic condition, which can include executing artificial intelligence and/or other algorithms.

20 Claims, 7 Drawing Sheets

Related U.S. Application Data which is a continuation of application No. 14/490,344, filed on Sep. 18, 2014, now Pat. No. 9,152,767, which is a continuation-in-part of application No. 13/930,353, filed on Jun. 28, 2013, now Pat. No. 8,856,053, which is a continuation of application No. 12/726,327, filed on Mar. 17, 2010, now Pat. No. 8,478,698.

(51) Int. Cl.

| | | |
|---|---|---|
| A61B 1/00 | (2006.01) | |
| A61B 1/24 | (2006.01) | |
| A61C 7/08 | (2006.01) | |
| A61B 1/04 | (2006.01) | |
| A61C 9/00 | (2006.01) | |
| G06F 19/00 | (2011.01) | |

(52) U.S. Cl.
CPC .............. *A61B 1/04* (2013.01); *A61B 1/24* (2013.01); *A61C 7/08* (2013.01); *A61C 9/0053* (2013.01); *G06F 19/325* (2013.01); *G06F 19/345* (2013.01); *G06F 19/3437* (2013.01)

(56) References Cited

U.S. PATENT DOCUMENTS

| 8,478,698 | B1* | 7/2013 | Mah ............................ 706/12 |
|---|---|---|---|
| 2002/0006217 | A1* | 1/2002 | Rubbert et al. ............. 382/131 |
| 2002/0015934 | A1* | 2/2002 | Rubbert et al. ............. 433/29 |
| 2002/0026105 | A1* | 2/2002 | Drazen ........................ 600/300 |
| 2002/0150859 | A1* | 10/2002 | Imgrund et al. ............. 433/24 |
| 2002/0180760 | A1* | 12/2002 | Rubbert et al. ............. 345/630 |
| 2003/0215764 | A1* | 11/2003 | Kopelman et al. ........... 433/24 |
| 2003/0219692 | A1* | 11/2003 | Kopelman et al. ........... 433/24 |
| 2004/0029068 | A1* | 2/2004 | Sachdeva et al. ............. 433/24 |
| 2005/0186526 | A1* | 8/2005 | Stewart et al. ................ 433/24 |
| 2006/0147872 | A1* | 7/2006 | Andreiko ..................... 433/24 |
| 2006/0263739 | A1* | 11/2006 | Sporbert et al. ............. 433/24 |
| 2009/0098502 | A1* | 4/2009 | Andreiko ..................... 433/24 |
| 2009/0246726 | A1* | 10/2009 | Chelnokov et al. ........... 433/24 |
| 2011/0129786 | A1* | 6/2011 | Chun et al. ................... 433/19 |
| 2013/0066598 | A1* | 3/2013 | Fisker et al. .................. 703/1 |
| 2013/0273491 | A1* | 10/2013 | Isaacson et al. .............. 433/24 |
| 2014/0067335 | A1* | 3/2014 | Andreiko ........................ 703/1 |

OTHER PUBLICATIONS

Ahmed El-Bial, "Towards a Complete Dental Treatment System", 2008, Proceedings of the 2008 CIBEC, pp. 1-8.*

Giordano et al., "Automatic Landmarking of Cephalograms by Cellular Neural Networks", 2005, AIME, pp. 3333-342.*

Kawahata et al., "A Measure of Agreement Between Clinicians and Computer-Based Decision Support System for Planning Dental Treatment", Sep. 2001, Journal of Dental Education, pp. 1031-1037.*

Noroozi, "Orthodontic Treatment Planning Software", 2006, American Journal Orthodontic Dentofacial Orthop, vol. 129, pp. 834-837.*

Sinthanayothin et all, "Orthodontics Treatment Simulation by Teeth Segmentation and Setup", 2008, Proceedings of ECIT-Con, pp. 81-84.*

Zarei et al, "An Intelligent System for Prediction of Orthodontic Treatment Outcome", Jul. 21, 2006, Internation Joint Conference on Neural Networks, pp. 2702-2706.*

Yagi et al., "Decision Making Models Compatible with Digital Associative Processor for Orthodotic Treatment Planning", 2009, IEEE, pp. 149-152.*

* cited by examiner

Root Tip Analysis (Degrees)

| Tooth # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Mesial | | | | | | | | 2 | 2 | | | | | | | |
| Distal | | | | | 5 | | | | | | | | 8 | | | |

| Tooth # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Mesial | | | | | | | | 2 | 2 | | | | | | | |
| Distal | | | | | | 2 | | | | | 2 | | | | | |

FIGURE 3

Tooth Torque Analysis (Degrees)

| Tooth # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Positive | | | | | | | 10 | 10 | 10 | 10 | | | | | | |
| Negative | | | | | | | | | | | | | | | | |

| Tooth # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Positive | | | | | | | | | | | | | | | | |
| Negative | | | | | | | | | | | | | | | | |

FIGURE 4

Arch Length Analysis (Millimeters)

| | Right "E" Space | Right Leeway Space | Right Posterior | Right Anterior | Left Anterior | Left Posterior | Left "E" Space | Left Leeway Space |
|---|---|---|---|---|---|---|---|---|
| Maxilla | | | 1 | 2 | 1 | 1 | | |
| Mandible | | | 1 | 3 | 2 | 1 | | |

FIGURE 5

METHODS AND SYSTEMS FOR EMPLOYING ARTIFICIAL INTELLIGENCE IN AUTOMATED ORTHODONTIC DIAGNOSIS AND TREATMENT PLANNING

FIELD OF THE INVENTION

The field of the present invention generally relates to methods and systems that may be used to diagnose an orthodontic condition. More particularly, the field of the present invention relates to methods and systems for automatically diagnosing, and proposing a treatment for, an orthodontic condition, which methods and systems employ the use of artificial intelligence capabilities.

BACKGROUND OF THE INVENTION

Many systems and methods have been developed or, more typically, envisioned which, hypothetically, could automate the capture of patient data and diagnosis of an orthodontic condition. These actual (or contemplated) systems employ certain components and subsystems that may automate the capture of patient data (such as orthodontic images or scans), the transfer of such data to an orthodontist, and/or even the interpretation of such data (or, more typically, discrete portions of such data). However, the currently-available methods and systems fail to comprise an ability to make decisions based on interpreted data, in an automated fashion. In other words, the currently-available methods and systems do not comprise an effective, accurate, and efficient "artificial intelligence" capability, in the automated diagnosis and treatment of an orthodontic condition.

The present invention addresses these shortcomings of the currently-available systems for automated orthodontic diagnosis and treatment.

SUMMARY OF THE INVENTION

A method for diagnosing and identifying a treatment for an orthodontic condition can include providing an imager configured for use by a patient, receiving patient data regarding the orthodontic condition such as onto a server, the patient data comprising data from an intraoral image initiated by the patient, accessing a database that comprises or has access to information derived from orthodontic treatment, generating an electronic model of the orthodontic condition by defining at least two anatomic features of a set of teeth, analyzing the patient data and identifying at least one diagnosis of the orthodontic condition based on the information derived from orthodontic treatments, executing an algorithm based on one or more inputs derived from the information derived from orthodontic treatments, identifying at least one treatment regimen for the at least one diagnosis, the at least one treatment regimen including at least one of a treatment approach, a corrective appliance and a combination thereof; and outputting the at least one treatment regimen to the patient.

A method for diagnosing and identifying a treatment for an orthodontic condition can include receiving patient data regarding an orthodontic condition, accessing a database, such as a database that comprises or has access to information derived from one or more patient treatments, and generating or otherwise building a model of an orthodontic condition, which can include defining one or more anatomic features of a set of teeth. A method can include analyzing patient data, identifying at least one diagnosis of an orthodontic condition, such as based on information derived from patient treatments, and executing one or more algorithms, such as an artificial intelligence algorithm, based on an input, which can include one or more inputs derived from information derived from a patient treatment. A method can include identifying at least one treatment regimen for a diagnosis, which can include identifying or otherwise outputting at least one of a treatment approach, a corrective appliance and a combination thereof, in whole or in part. A method can include instructing a computer or other software program to perform one or more method steps. A method can include tagging or otherwise designating one or more anatomic features of teeth with an electronic identifier, such as an identifier generated by an algorithm, an identifier defined by a user, a combination thereof, or another identifier. An anatomic feature of a tooth can include any of incisal edges, cusp tips, occlusal fossa, points of maximum crown convexity, marginal ridges, interproximal contact points, interocclusal contact points, interdental papilla heights, marginal gingival lines, zones of attached gingiva and combinations thereof.

A method can include aligning or otherwise disposing or moving one or more anatomic features, which can include aligning one or more anatomic features based on a pattern, such as a pattern representing a target or other orthodontic condition, which can be or include at least one of an ideal condition, an acceptable condition, such as a condition based on one or more previously successful patient treatments, other conditions, and a combination thereof. A method can include aligning one or more anatomic features in one or more ways, which can include disposing one or more anatomic feature identifiers along or otherwise relative to a curve, a spline, one or more additional anatomic feature identifiers, or other references, such as within a model. A method can include aligning one or more anatomic features on an arch relative to one or more anatomic features on another arch, or on the same arch.

A method can include transmitting, receiving or otherwise communicating data, such as patient data, treatment data or other data, through or via a website, which can include transmitting, receiving or otherwise communicating data to and/or from a server or other computer(s), directly, indirectly or otherwise. One or more databases can include and/or have access to treatment data, such as patient treatment information or other information, which can include information from at least one of textbooks, scientific literature, results derived from ongoing patient treatments, results derived from completed patient treatments and a combination thereof. A method can include estimating, assigning or otherwise identifying a probability value associated with one or more diagnoses, such as a probability value that can represent a likelihood that one or more diagnoses are accurate.

A system for diagnosing and identifying a treatment for an orthodontic condition can include one or more servers, which can be adapted to receive, transmit or otherwise process or communicate data, such as patient data, treatment data or other information. A system can include one or more databases, which can include and/or have access to information relating to patient treatments. A system can include one or more electronic models of one or more orthodontic condition, such as a model that defines or otherwise represents one or more anatomic features of a set of teeth. A system can include one or more computer, software or other programs or applications, which can be housed within and/or accessible by a server, database or other system component. A system application or other component can be adapted to analyze information, such as patient data and data relating to one or more patient treatments, and to estimate or otherwise identify one or more diagnoses of an orthodontic condition. A system can include an application or other component adapted to execute one or more algorithms, such as artificial intelligence and/or other algorithms, which can include being adapted to execute algorithms based on one or more inputs, such as inputs derived from or otherwise based on patient treatments, the results of patient treatments or other information. A system application or other component can be adapted to recommend or otherwise identify one or more treatment regimens for one or more diagnoses, such as a treatment approach or other method, a corrective appliance, or a combination thereof. Alternatively, or collectively, a system application or other component can be adapted to recommend or otherwise identify one or more treatment regimens that may not be appropriate, suitable or otherwise applicable for one or more diagnoses.

A system can include one or more identifiers for an anatomic feature of a tooth or set of teeth, which can include one or more electronic identifiers for one or more anatomic features, such as identifiers generated by an algorithm, identifiers defined by a user, identifiers otherwise defined or existing in a system application, or a combination thereof. A system can include one or more identifiers for any anatomic feature of a tooth or set of teeth, such as incisal edges, cusp tips, occlusal fossa, points of maximum crown convexity, marginal ridges, interproximal contact points, interocclusal contact points, interdental papilla heights, marginal gingival lines and zones of attached gingiva, separately or in combination, in whole or in part. A system application or other component can be adapted to align or otherwise dispose one or more anatomic features or identifiers to, from, between or otherwise among one or more positions, which can include manipulating one or more anatomic features relative to one another, relative to or otherwise based on a pattern, such as a template representing a target orthodontic condition, along or otherwise relative to a curve, spline, or other shape, or relative to one or more other anatomic features, such as features defined or within a model, separately or in combination, in whole or in part.

A system can include one or more websites, such as a website adapted to receive or otherwise process patient data or other input, and one or more servers, such as a server adapted to communicate with one or more other system components, which can include being adapted to receive, transmit or otherwise process patient data or other information, such as information from, to or through one or more websites. One or more websites can be hosted on one or more servers within a system. A system can include one or more databases that can include and/or have access to patient treatment information and/or other information, such as information from or otherwise based on textbooks, scientific literature, results of ongoing patient treatments, or results of completed patient treatments, separately or in combination, in whole or in part. A system can include an application or other component adapted to estimate, assign or otherwise identify a probability value associated with one or more diagnoses, such as a probability value that can represent a likelihood that one or more diagnoses are accurate.

A computer readable medium can have instructions stored thereon that, when executed by a processor, can cause the processor to perform one or more of the methods of the present disclosure, separately or in combination, in whole or in part. A computer readable medium can have instructions stored thereon that, when executed by a processor, can cause the processor to perform a method that can include receiving data regarding an orthodontic or other condition, such as on or by one or more servers, accessing or otherwise communicating with a database, such as a database comprising or having access to treatment or other patient information, generating a model, such as an electronic or electronically stored model, of one or more orthodontic conditions, defining one or more anatomic features of a tooth or set of teeth, analyzing patient or other data, identifying one or more diagnoses of an orthodontic condition, executing one or more algorithms, such as artificial intelligence or other algorithms, processing one or more inputs, such as input derived from patient treatments, and identifying one or more treatment regimens for one or more diagnoses, such as a treatment regimen including at least one of a treatment approach, a corrective appliance and a combination thereof.

The above-mentioned and additional features of the present invention are further illustrated in the Detailed Description contained herein.

BRIEF DESCRIPTION OF THE FIGURES

FIG. 3: a table summarizing the results of a root tip analysis of a patient.

FIG. 4: a table summarizing the results of a tooth torque analysis of a patient.

FIG. 5: a table summarizing the results of an arch length analysis of a patient.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention. The figures will be described in conjunction with one another.

Figure 1:
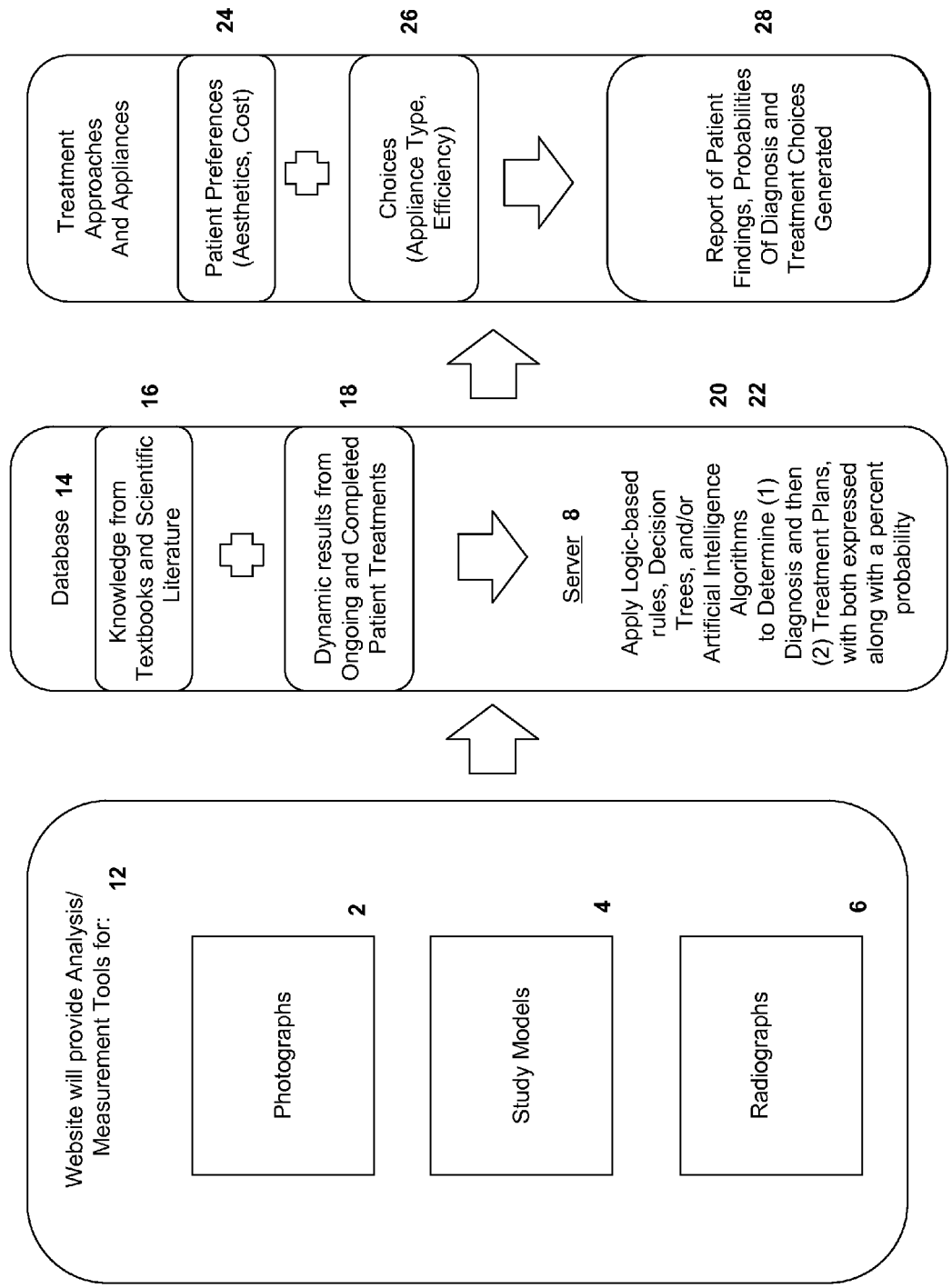
FIG. 1: a diagram illustrating the general steps and processes encompassed by the present invention, namely, the generation of patient data, the analysis of such data by one or more servers, and the automated diagnosis of an orthodontic condition and the proposed treatment approaches therefor.

Referring to FIG. 1, according to certain embodiments of the present invention, automated diagnosis of an orthodontic condition begins with the production of patient-specific data, which may comprise patient photographs 2, study models 4, radiographs 6, and/or combinations thereof. The types of data captured for a particular patient may be the same for all patients, or may be customized for each patient. The "orthodontic condition," referenced herein, may generally comprise an arrangement of a patient's teeth that is undesirable according to applicable orthodontic standards, whereby such arrangement may be undesirable for medical, orthodontic, aesthetic, and other reasons. Examples of such orthodontic conditions include, but are not limited to, overbites, crossbites, openbites, overjets, underbites, and the like.

Figure 2:
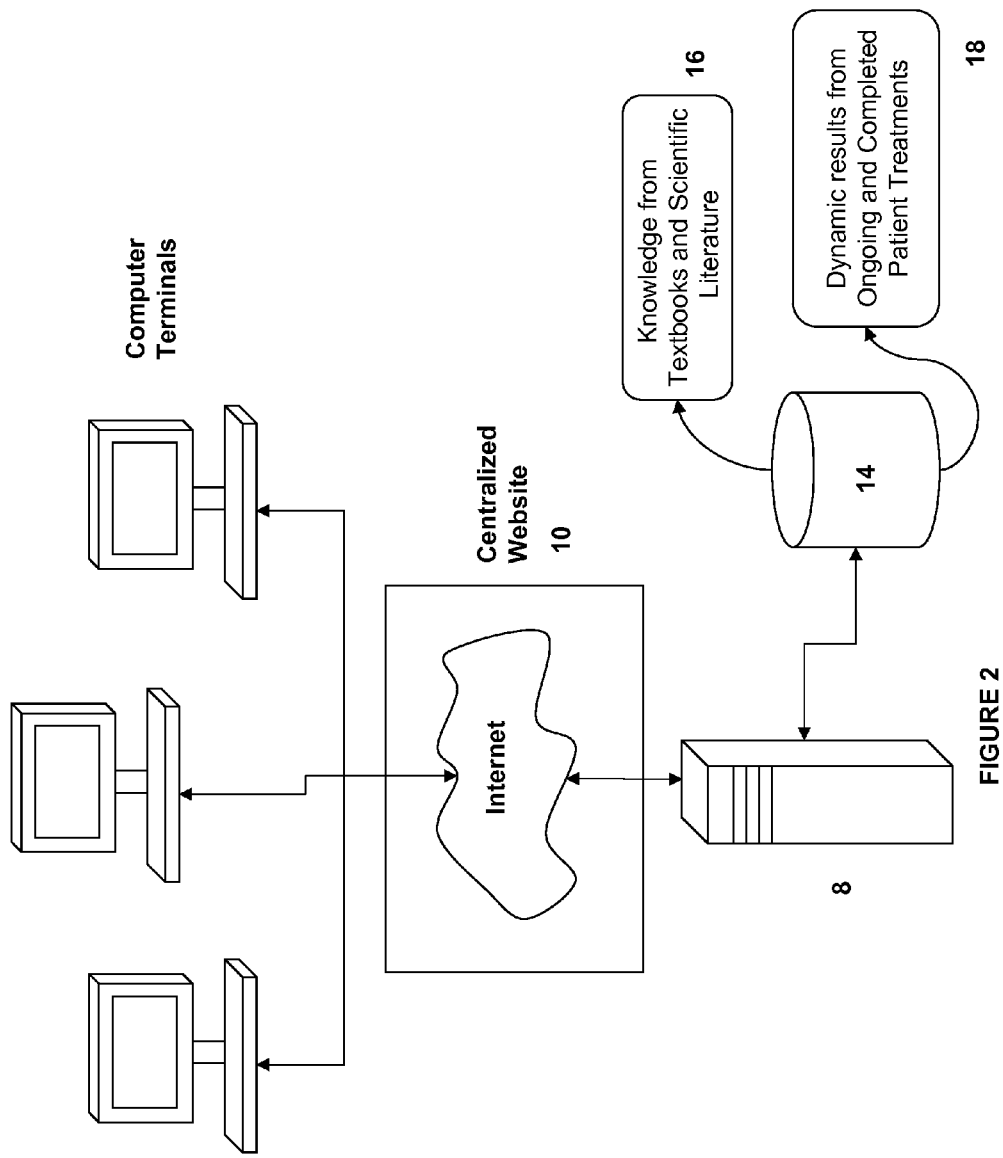
FIG. 2: a diagram illustrating the various components of the systems described herein, namely, the centralized website, server, and database described herein.

These patient data may then be provided to a server 8 through a centralized website 10. Referring to FIG. 2, such data may be provided to the server 8 vis-à-vis an on-line form (within a centralized website 10) through which the data may be uploaded and transferred to the server 8, or through a constant data feed through a standard Internet connection. As described herein, the server 8 will preferably comprise certain tools 12 for analysis and interpretation of such data—and for making intelligent and probabilistic diagnosis and proposed treatments for an orthodontic condition.

The invention provides that the server 8 will preferably be capable of communicating with at least one database 14 (or group of databases). The database 14 will preferably store and/or have access to knowledge and information derived from scientific, medical, and orthodontic textbooks and literature 16. More particularly, the invention provides that a single database 14 may store all of such information—or, alternatively, it may store portions of such information and the server 8 may have access to additional information that may be stored within other databases.

According to certain preferred embodiments, the invention will preferably employ a systematic approach to evaluating the strength of scientific evidence that may be retrieved from the database 14 described herein, for the purpose of diagnosing an orthodontic condition (as described below). For example, the server 8 may consider the quality, quantity and consistency of the evidence to derive a grade or confidence level of the available knowledge. The invention provides that various criteria, such as indirect supporting evidence, may be taken into account in assessing the strength of each piece of scientific evidence. The scientific evidence may then be ranked, based on the grade levels (or confidence levels) assigned thereto.

More particularly, for example, the invention may consider the strongest evidence (i.e., evidence of higher grade levels) being derived from at least one systematic review of one or more well-designed and randomized controlled trials. The invention provides that a second highest grade may be assigned to, for example, evidence derived from at least one properly designed randomized controlled trial, which involved an appropriate sample size and statistical power. The invention further provides that a third highest grade may be assigned to evidence derived from well-designed trials, without randomization; a single group pre-post, cohort, time series study; or matched case-controlled studies. Still further, the invention provides that a fourth grade may be assigned to evidence from well-designed, non-experimental studies, carried out by more than one center or research group. A fifth and lowest grade of evidence may consist of opinions of respected authorities (which are based on clinical evidence), and/or descriptive studies or reports of expert committees.

The invention provides that the database 14 will further comprise, or have access to, information that represents dynamic results from ongoing and previously completed orthodontic studies 18. Preferably, these dynamic results 18 will be organized by orthodontic condition, such that the most relevant information may be retrieved as quickly as possible, within the database 14. Similar to the information derived from scientific, medical, and orthodontic textbooks and literature 16, the invention provides that all of the dynamic results 18 may be stored within the database 14 or, alternatively, portions thereof may be stored within the database 14 and other dynamic results 18 may be retrieved, as needed, from third party databases.

Upon providing the server 8 with the patient data, e.g., patient photographs 2, study models 4, radiographs 6, and/or combinations thereof, a user may instruct the server 8 to conduct an automated diagnosis. The automated diagnosis will be based upon the patient data, the information derived from scientific textbooks and literature 16, and dynamic results from ongoing and previously completed orthodontic studies 18. The server 8 will preferably employ the use of logic-based rules and decision trees 20 to diagnose an orthodontic condition based on all of such information. The invention provides that the server 8 will preferably express the diagnosis by identifying one or more orthodontic conditions, along with a probability value for each orthodontic condition. According to such embodiments, the probability value would represent the relative probability that the diagnosis is accurate.

Still further, the server 8 will be configured to output (recommend) one or more treatment approaches and/or corrective orthodontic appliances 22. More particularly, for each diagnosis 20 identified by the server 8, the server 8 will propose one or more treatment approaches, corrective appliances, or combinations thereof 22. The invention provides that each such proposed treatment approach and corrective appliance will be correlated with a probability value. The invention provides that this probability value will represent the probability of the proposed treatment approach and/or appliance correcting the diagnosed orthodontic condition.

The invention further provides that a user may input patient preferences 24 and/or orthodontist-specified preferences to the server 8 (through the centralized website 10). For example, the invention provides that a patient may filter the proposed treatments and corrective appliance results 26 based on cost, or the relative aesthetics of an appliance. Similarly, an orthodontist may filter the proposed treatments and corrective appliance results 26 based on his/her bias—e.g., an orthodontist may instruct the server 8 to only consider, or to not consider, a certain type of corrective appliance. Upon completion of the foregoing process, the server may be instructed to generate a report 28, which preferably summarizes the patient data, the diagnoses and associated probability values, the proposed treatment approaches and/or corrective devices (and the probability values associated therewith), and any patient and orthodontist preferences that were considered during the analysis.

According to certain embodiments, the invention provides that the server 8 is configured to analyze the patient data by identifying a location and position of a plurality of teeth in the patient data in two-dimensional space or, even more preferably, in three-dimensional space (provided that the type and amount of patient data provided to the server 8 is sufficient to do so). The invention provides that the server 8 may be configured to undertake this analysis automatically or, according to certain embodiments, the centralized website 10 will provide users with certain on-line tools to specify the location and position of the plurality of teeth in the patient data. For example, such on-line tools may be used to identify, within the patient data, the location and position of a patient's incisors, canines, premolars and molars, as shown within the patient data that has been provided to the server 8. The location, position, contours, and size of the plurality of teeth may be mapped out by such user within the centralized website 10, while the user is viewing the patient data that has been uploaded to the server 8, e.g., using a graphics tool that allows a user to, for example, approximately trace or identify the outer boundaries of each tooth.

According to such embodiments, the server 8 may be further configured to assign coordinates to each tooth within the plurality of teeth. The invention provides that such coordinates are preferably correlated to the location and position of each tooth, as automatically determined by the server (or as otherwise identified by a clinician, using the on-line patient data analysis tools, described above). According to these embodiments, the invention provides that the coordinates for each of the plurality of teeth may then be compared (by the server 8) to a table contained within the database 14. The table will preferably comprise a series of diagnostic data sets, with each diagnostic data set comprising coordinates, or a range of coordinates, which are correlated with (1) a known location and position of a plurality of teeth and (2) a previously diagnosed orthodontic condition (which previous diagnoses are derived from (a) information derived from textbooks and scientific literature and (b) dynamic results derived from ongoing and completed patient treatments).

According to such embodiments, the server 8 may then be instructed to identify a diagnostic data set contained within the database 14 that represents a statistical "best fit," or most closely resembles, the coordinates for the plurality of teeth of the patient. At this point, the server 8 may be instructed to diagnosis the orthodontic condition based on the "best fit" diagnostic data set that it identified. As mentioned above, the server 8 may further assign a probability value to this diagnosis. The probability value will preferably be based, at least in part, on a confidence level that has been assigned to the diagnostic data set which the server identifies as the statistical best fit for the coordinates for the plurality of teeth of the patient. This confidence level will preferably be influenced by the grade level that is assigned to the evidence that supports a connection between the orthodontic condition that is correlated with the particular diagnostic data set, as described above.

According to certain embodiments, the server 8 or, more particularly, the computer program housed therein, may be instructed to identify at least one treatment approach, a corrective appliance, or a combination thereof for the at least one diagnosis that is derived from the patient's data. This step may be carried by, for example, instructing the server 8 to calculate a set of target coordinates, which represent a desired and corrected location and position of each tooth in the plurality of teeth of the patient. Based on the target coordinates, the current location and position coordinates of the patient's teeth, and the diagnosed orthodontic position, the server 8 may be instructed to identify at least one treatment approach, a corrective appliance, or a combination thereof, which will be effective to reorient the plurality of teeth towards the location and position represented by the target coordinates. The server 8 may further be instructed to calculate a probability value that is correlated with a relative likelihood of the at least one treatment approach, corrective appliance, or a combination thereof, being effective to reorient the plurality of teeth to a location and position represented by the target coordinates.

According to certain preferred embodiments, the invention will preferably employ certain additional algorithms in analyzing patient data, diagnosing orthodontic conditions and probability values therefor, and proposing treatment approaches and corrective appliances (and probability values therefor). By way of illustration, as mentioned above, the server 8 may be configured to assign greater value (weight) to existing scientific and medical knowledge, relative to dynamic results from ongoing and completed treatments—when diagnosing and providing recommended treatment protocols for patients. The following will describe certain non-limiting examples of algorithms, which may be employed in the processes and systems of the present invention.

The invention provides that artificial intelligence algorithms will preferably be employed in order to create an artificial neural network, which will enable the server to perform the orthodontic diagnosis, treatment planning and prognostication steps described herein. The algorithms may utilize statistical estimation, optimization and control theory methodology, or combinations thereof. In the case of statistical estimation methods, estimators and estimation methods that may be employed include, but are not limited to, the following: maximum likelihood estimators, Bayes estimators, method of moments estimators, Cramer-Rao bound, minimum mean squared error (also known as Bayes least squared error), maximum a posteriori, minimum variance unbiased estimator, best linear unbiased estimator, unbiased estimators, particle filter, Markov chain Monte Carlo, Kalman filter, Ensemble Kalman filter, and Wiener filter. The statistical optimization techniques that may be utilized include single-variable optimizations or, more preferably, multi-variable optimization techniques. The statistical optimization methods may include, but are not limited to, the following: Bundle methods, Conjugate gradient method, Ellipsoid method, Frank-Wolfe method, Gradient descent (also known as steepest descent or steepest ascent), Interior point methods, Line search, Nelder-Mead method, Newton's method, Quasi-Newton methods, Simplex method and Subgradient method.

Because the systems and methods of the present invention involve certain input provided by users of the invention, the systems and methods are dynamic. As such, the invention provides that algorithms that employ control theory may be employed to solve problems in connection with the orthodontic diagnosis, treatment planning and prognostication steps described herein. Non-limiting examples of such control theory methods include: Adaptive control, Hierarchical control, Intelligent control, Optimal control, Robust control and Stochastic control.

EXAMPLES

Example of Optimization Algorithm for Decision Making in Diagnosis and Treatment Planning. An important aspect of multiple optimization is the handling of human preferences, such as the type of cost- and aesthetic-related preferences that a patient or orthodontist may provide to the system described herein. Although selection or prioritizing alternatives from a set of available options with respect to multiple criteria termed Multi-Criteria Decision Making (MCDM) is an effective optimization approach, in practical applications, alternative ratings and criteria weights can not always be precisely assessed due to unquantifiable, incomplete, and/or unobtainable information—or because of a lack of knowledge that may cause subjectiveness and vagueness in decision performance. As such, the invention provides that the application of fuzzy set theory to MCDM models provides an effective solution for dealing with subjectiveness and vagueness commonly found with clinical information. In such embodiments, the invention provides that human preferences—from both patient and clinician—may be assigned "utility values" in which a scaled real number is assigned to indicate its relative importance. The resulting weighting vector, which evaluates criteria of decision making, is then provided in fuzzy linguistic terms such as very poor, poor, fair, good, and very good.

Example of Decision Tree Algorithm for Decision Making in Diagnosis and Treatment Planning. The invention provides that a decision tree method referred to as "C4.5," which allows for input of continuous numerical data, is preferably employed in the methods and systems described herein. The invention provides that, under this approach, a decision tree may be "learned" vis-à-vis splitting a source set into subsets, based on an attribute value test. The invention provides that this process may be repeated on each derived subset in a recursive manner, which is completed when the subset (at a node) has the same value of the target variable, or when splitting no longer adds value to predictions. According to this embodiment, decision trees are used for relatively simpler functions as decision-tree learners create over-complex trees (overfitting), although pruning may, optionally, be performed to minimize this problem. In addition, concepts that are relatively more difficult to learn are not easily expressed by decision trees—and, in such case, more advanced algorithms will be implemented in the systems and methods described herein.

Example of Partially Observable Markov Decision Processes (POMDPs) and Variants Thereof. The invention provides that POMDPs are preferably used in the clinical applications described herein, particularly for decisions that are made based on incomplete information. The invention provides that POMDPs are preferably advantageous insofar as they facilitate the combination of patient data, e.g., patient data derived from examination, photographs, radiographs and any other diagnostic aids—as well as the current state of knowledge of the cause-and-effect representation from these data and measurements. The invention provides that feature selection may be performed using pattern recognition techniques and, furthermore, the treatment decisions with which to restore the patient to a more desirable or ideal state are produced.

Patient Example. The following example describes the application of the processes described herein to a patient in need of orthodontic diagnosis and treatment. The process begins with the patient undergoing cephalometric radiographic analysis. The data generated by such analysis are presented in the table below.

| Measurement | Patient |
| --- | --- |
| SNA (degrees) | 82° |
| SNB (degrees) | 74° |
| ANB (degrees) | 8° |
| Maxillary incisor to NA (degrees) | 22° |
| Maxillary incisor to NA (millimeters) | 6 mm |
| Mandibular incisor to NB (degrees) | 24° |
| Mandibular incisor to NB (millimeters) | 4 mm |
| Pogonion to NB (millimeters) | 4 mm |
| Maxillary incisor to Mandibular incisor (degrees) | 140° |
| Occlusal plane to SN (degrees) | 15° |
| Go-Gn to SN (degrees) | 32° |
| Mandibular incisor to MP (degrees) | 86° |

Those of ordinary skill in the art will appreciate that the cephalometric radiographic analysis may be performed to capture measurements, other than those specified above. However, the measurements summarized in the table above are often important to any orthodontic diagnosis and treatment. Next, the patient's dentition may be analyzed and measured. The table below provides a summary of the results of such analysis and, specifically, the analysis of the patient's anteroposterior and vertical movements.

| | Right Molar | Right Canine | Midline | Left Canine | Left Molar |
| --- | --- | --- | --- | --- | --- |
| Anteroposterior Movements (mm) | | | | | |
| Maxilla | | | 1.5 mm left | 1.0 distal | |
| Mandible | 3 mesial | 2.5 mesial | 0.5 mm left | 2 mesial | 3 mesial |
| Vertical Movements (mm) | | | | | |
| Maxilla | | 1.5 mm occlusal | | 2.0 mm occlusal | |
| Mandible | | | | | |
| Curve of Spee (mm) | | | | | |
| Maxilla | | | | | |
| Mandible | | | 3 mm | | |

The diagnostic process of this Example further entails the following analyses of the patient: (1) a root tip analysis (results are summarized in FIG. 3); (2) a tooth torque analysis (results are summarized in FIG. 4); (3) an arch length analysis (results are summarized in FIG. 5); and (4) a Bolton analysis (the results of which are summarized in the table below).

| Bolton Analysis (Millimeters) | | |
| --- | --- | --- |
| | Anterior (Bolton 6) mm | Posterior (Bolton 12) mm |
| Maxilla Mandible | 2 mm deficient | 2 mm deficient |

The invention provides that a series of image analyses may then be performed, namely, an image analysis of a patient's frontal and profile planes. The results captured in this Example are summarized in the tables below.

| Frontal Analysis | |
| --- | --- |
| Parameter | Results |
| Upper Third | Within normal limits |
| Middle Third | Within normal limits |
| Lower Third | Decreased |
| Maxillary Lip | Within normal limits |
| Mandibular Lip | Within normal limits |
| Smile | Within normal limits |
| Gingival Display | Within normal limits |
| Symmetry | Within normal limits |

| Profile Analysis | |
| --- | --- |
| Parameter | Results |
| Profile | Convex |
| Maxillary lip to E plane | 1 mm |
| Lip strain | Yes |
| Lip competence | Incompetent |

As explained above, the invention provides that a patient and/or clinician (dentist or orthodontist) may specify certain additional criteria, which the server will consider in calculating a diagnosis and treatment plan. The table below provides the criteria selected by the patient in this Example.

| Patient Preferences | |
|---|---|
| Parameter | Priority (Scale of 1-10 for Importance) |
| Facial Aesthetics | 9 |
| Comfort | 2 |
| Treatment Time | 7 |
| Removable Appliances | 1 |
| Aesthetic Braces | 2 |
| Orthognathic Surgery | 1 |
| Cost | 5 |

The foregoing patient data, measurements, and preferences are subsequently provided to the server, via the centralized website described herein. Using one or more artificial intelligence algorithms, such as the algorithms described herein (or combinations thereof), as well as (i) information derived from textbooks and scientific literature and (ii) dynamic results derived from ongoing and completed patient treatments, the server calculates one or more diagnoses for the patient, along with an associated probability value (which is indicative of the relative accuracy of each diagnosis). Three diagnoses, and associated probability values, for this Example are listed below.

Diagnosis One: Class II Malocclusion (85%)
Diagnosis Two: Class I Malocclusion (14%)
Diagnosis Three: Class III Malocclusion (1%)

In addition, based on the foregoing patient data, measurements, preferences, information, and diagnoses, the server calculates one or more proposed treatment regimens for the patient, along with a probability value that is correlated with a relative likelihood of the relevant treatment approach, corrective appliance, or a combination thereof, being effective to reorient the patient's teeth to the desired location and position. The list of proposed treatment regimens, and corresponding probability values, calculated in this Example is provided below.

Growth Modification (61%)
Mandibular Extractions (72%)
Maxillary Extractions (58%)
Removable Appliances (8%)
Fixed Appliances (92%)
Retainers (99%)

In this Example, the server further calculated the average probably treatment time to be about 26.5 months.

In at least one embodiment, patient data can include anatomic information regarding one or more teeth, such as information regarding an anatomic feature(s) of one or more teeth in a set of teeth (e.g., a full set or a partial set). Examples of such anatomic features can include incisal edges, cusp tips, occlusal fossa, points of maximum crown convexity, marginal ridges, interproximal contact points, interocclusal contact points, interdental papilla heights, marginal gingival lines and zones of attached gingiva, among others, separately or in combination, in whole or in part. The anatomic information or data can be provided or stored in any manner according to a particular application, which can include being stored within database 14 or otherwise disposed for communication with server 8, such as by way of a website (which can be hosted on server 8 or elsewhere), peer-to-peer computer connection, File Transfer Protocol (FTP), direct device-to-computer connection or other communication system, such as an indirect, wired, wireless or other system, separately or in combination. In at least one embodiment, anatomic data can include one or more tags, such as electronic tags or other electronic identifiers, assigned to anatomic features of a patient's teeth for defining a location or other attribute thereof (e.g., within a 2D or 3D model). The tags can be assigned in any manner according to a particular application, such as manually, automatically or otherwise. For example, one or more tags can be applied by a user, such as by way of numerical or other inputs provided manually or in another manner. In at least one embodiment, tags can be provided through a Graphical User Interface (GUI), such as a GUI provided on a website (if present), which can, but need not, include point-and-click input capabilities. Alternatively, or collectively, tags can be defined by one or more algorithms executed by a processor, such as a processor running software associated with server 8 and/or database 14.

One or more computer models can be generated based on the tags and/or other anatomic information, whether separately or in combination with one another or with one or more of the other types of data discussed elsewhere herein. For example, an electronically stored model, such as an electronic virtual treatment model or automated tooth setup, of an orthodontic condition or malocclusion can be produced based on the anatomic and/or other data and one or more algorithms (e.g., the artificial intelligence and other algorithm described herein) can be executed to calculate a proposed treatment regimens (e.g., approaches, appliances, etc.) for improving the malocclusion represented by the model(s). In at least one embodiment, two or more models can be wholly or partially compared, such as by comparing a virtual treatment model to a target model representing a corrected or improved set of teeth, and a proposed treatment regimen can include one or more recommendations for transforming at least a portion of the virtual treatment model into a corresponding portion of the target model. A target model can include, for example, a model representing a visual treatment objective (VTO), a surgical treatment objective (STO), or another objective, separately or in combination, in whole or in part.

In at least one embodiment, the tags and/or other anatomic information (separately or in combination with other data) can be used to align one or more anatomic features within a model relative to one another and/or relative to a pattern or other target configuration. For example, a tag or set of tags corresponding to an orthodontic condition can be arranged, rearranged or otherwise processed (e.g., via one or more algorithms) to follow a pattern based on known information, such as a pattern established historically. A historic pattern or other configurations can be or include, e.g., an ideal configuration, an improved configuration or another configurations, such as an arrangement based on a consensus of previous, successful patient treatments. Such configurations can be based on any number of factors according to a particular application; for instance, an ideal or improved configuration can be based on medical opinion, patient opinion, opinions regarding aesthetics, or other considerations, such as one or more of the factors described elsewhere in the present disclosure, separately or in combination, in whole or in part.

As other examples, the systems and methods of the present disclosure can line up incisal edges and cusp tips along a curve, such as a U-shaped or otherwise-shaped curve (whether symmetrical or asymmetrical), align marginal ridges relative to a spline, arrange (e.g., using tags) anatomic features on an arch relative to anatomic features on another arch, such as an opposing arch, or on the same arc, or both. Of course, the foregoing examples are for illustrative purposes and alternatively, or collectively, the systems and methods of the present disclosure can arrange any anatomic or other feature (in any number) associated with teeth relative to or otherwise in view of any other feature, reference point or location. Additionally, in at least one embodiment of Applicant's disclosure, one or more of the artificial intelligence and other algorithms disclosed herein can cooperate with the various components and inputs described above to automatically develop one or more routines and/or algorithms for correcting, improving or otherwise changing a malocclusion or other orthodontic condition according to an electronically stored model, such as an electronic virtual treatment model or automated tooth setup. Further, such routines and/or algorithms can change or otherwise affect one or more outputs over time, such as, for example, by providing progressively more accurate or effective proposed treatment regimens based on prior treatment regimens and results achieved by the prior treatment regimens.

According to certain aspects of the present invention, methods and systems for diagnosing and identifying a treatment for an orthodontic condition are provided. Such methods and systems generally can comprise the use of a server on which a centralized website can be hosted. The server can be configured to receive patient data through the website, with such patient data comprising patient photographs, study models, radiographs, and/or combinations thereof. The methods and systems can comprise the use of a database that includes or has access to information derived from, e.g., textbooks and scientific literature and results of ongoing and/or completed patient treatments. In at least one embodiment, at least one computer program can operate within a server, which can be capable of analyzing patient data and identifying at least one diagnosis of an orthodontic condition (e.g., based on the information derived from textbooks and scientific literature, dynamic results derived from ongoing and completed patient treatments, or combinations thereof). The methods and systems can comprise assigning a probability value to at least one diagnosis, wherein the probability value can represent a likelihood that a diagnosis is accurate. According to such embodiments, which are but some of many, the methods and systems can comprise instructing a computer program to identify at least one treatment approach, a corrective appliance, or a combination thereof for at least one diagnosis.

In at least one embodiment, a method for diagnosing and identifying a treatment for an orthodontic condition can include providing a server on which a centralized website is hosted, wherein the server is configured to receive patient data through the website, providing a database that comprises or has access to information derived from textbooks and scientific literature and dynamic results derived from ongoing and completed patient treatments, operating at least one computer program within the server, which is capable of analyzing the patient data and identifying at least one diagnosis of the orthodontic condition based on said information derived from textbooks and scientific literature and dynamic results derived from ongoing and completed patient treatments, assigning a probability value to the at least one diagnosis, wherein the probability value represents a likelihood that the diagnosis is accurate, and instructing the computer program to identify at least one treatment approach, a corrective appliance, or a combination thereof for the at least one diagnosis. A server can be configured to identify a location and position of a plurality of teeth in patient data in at least one of two-dimensional and three-dimensional space. A method can include assigning coordinates to one or more teeth within a plurality of teeth, wherein said coordinates can be correlated to a location and/or position of one or more teeth or portions thereof. A method can include comparing coordinates for teeth to a table contained within a database, such as a table that comprises a series of diagnostic data sets with each diagnostic data set comprising coordinates, or a range of coordinates, which can be correlated with a known location or position of a plurality of teeth and/or a previously diagnosed orthodontic condition, instructing a server to identify a diagnostic data set contained within a database, which can represent a statistical fit (e.g., best fit) or most closely resemble coordinates for one or more teeth of a patient, and instructing a server to diagnosis an orthodontic condition based on a diagnostic data set identified. A probability value can be assigned to at least one diagnosis based, at least in part, on a confidence level assigned to a diagnostic data set, such as a data set which a server can identify as a statistical best or other fit for coordinates for one or more teeth of a patient.

A method can include instructing a computer program to identify at least one treatment approach, a corrective appliance, or a combination thereof for at least one diagnosis, which can include instructing a server to calculate a set of target coordinates, which can represent a desired or corrected location or position of a tooth, and identifying at least one treatment approach, a corrective appliance, or a combination thereof, which can be at least partially effective to reorient one or more teeth toward a location or position represented by one or more target coordinates. A method can include instructing a server to calculate a probability value that can be correlated with a relative likelihood of at least one treatment approach, corrective appliance, or a combination thereof, being effective to reorient one or more teeth to a location or position represented by a target, and can include employing an application of at least one artificial intelligence or other algorithm. A method can include identifying at least one treatment approach, a corrective appliance, or a combination thereof for at least one diagnosis by employing an application of at least one artificial intelligence algorithm.

In at least one embodiment, a system for diagnosing and identifying a treatment for an orthodontic condition can include a server on which a centralized website is hosted, wherein the server is configured to receive patient data through the website, a database that comprises or has access to information derived from textbooks and scientific literature and dynamic results derived from ongoing and completed patient treatments, and at least one computer program housed within or accessible by the server, which is capable of analyzing the patient data and identifying at least one diagnosis of the orthodontic condition based on said information derived from textbooks and scientific literature and dynamic results derived from ongoing and completed patient treatments, wherein the server can be adapted for assigning a probability value to the at least one diagnosis, wherein the probability value represents a likelihood that the diagnosis is accurate, and instructing the computer program to identify at least one treatment approach, a corrective appliance, or a combination thereof for the at least one diagnosis. A server can be configured to identify a location or position of a plurality of teeth in patient data in at least one of two-dimensional and three-dimensional space, and can be configured to assign coordinates to one or more teeth, such as coordinates that can be correlated to a location or position of each tooth. A server can be configured to compare coordinates for one or more teeth to a table contained within a database, wherein the table can comprise a series of diagnostic data sets, such as one or more diagnostic data sets comprising coordinates, or a range of coordinates, which can be correlated with a known location or position of one or more teeth or a previously or otherwise diagnosed orthodontic condition. A server can be configured to identify a diagnostic data set contained within a database, which can represent a statistical best fit, or most closely resemble, coordinates for one or more teeth of a patient, and to diagnose an orthodontic condition based on a diagnostic data set.

A system can include a probability value assigned to at least one diagnosis, which can be based, at least in part, on a confidence level assigned to a diagnostic data set, such as a data set which the server can identify as a statistical best fit for the coordinates for one or more teeth, such as one or more teeth of a plurality of teeth of a patient. A system can include a computer program adapted to identify at least one treatment approach, a corrective appliance, or a combination thereof for at least one diagnosis, which can include instructing a server to calculate a set of target coordinates, which can represent a desired or corrected location or position of one or more teeth, and identify at least one treatment approach, a corrective appliance, or a combination thereof, which can be at least partially effective to reorient one or more teeth toward a location or position represented by one or more target coordinates. A server can be configured to calculate a probability value that can be correlated with a relative likelihood of at least one treatment approach, corrective appliance, or a combination thereof, being effective to reorient one or more teeth to a location or position represented by target coordinates. A server can be configured to employ at least one artificial intelligence or other algorithm when identifying at least one diagnosis of an orthodontic condition and/or when identifying at least one treatment approach, a corrective appliance, or a combination thereof for at least one diagnosis.

In at least one circumstance, an individual, such as a patient, consumer, or end user, can be interested in inquiring into or participating in self-improvement of a dental condition, such as dental alignment. For instance, a person can be interested in obtaining information regarding, or even devices for treating, an orthodontic condition without, or at least optionally without, incurring the time and expense that may be associated with obtaining care from a dentist or other medical professional. Such a person may be interested in obtaining information relating to cost, complexity, numbers or types of appliances, time, steps, treatment scenarios, active movement periods, rest periods, or other treatment details that may be associated with treatment options for their teeth, such as by way of dental aligners. In at least one embodiment, one or more of the systems and methods of the present disclosure can provide a person with such an opportunity, which can include providing an individual with treatment related information and options, and an ability to choose a treatment or treatment plan that suits their needs or preferences, such as on the bases of treatment type, time, affordability, or other considerations relevant to dental treatment.

Figure 6:
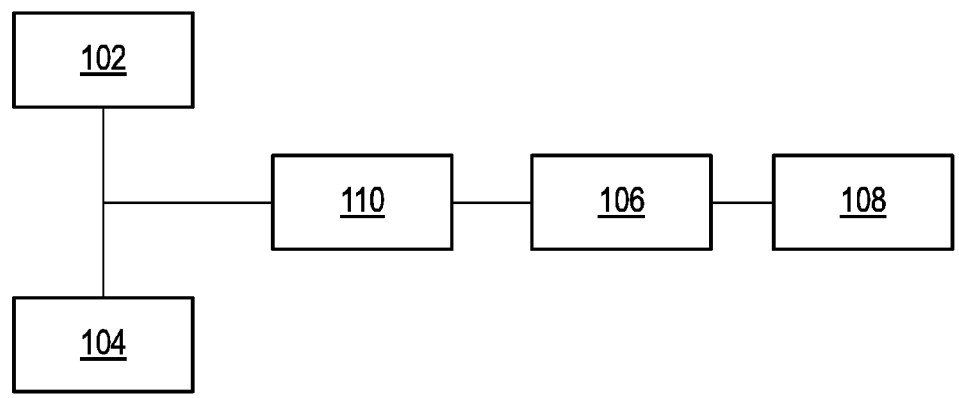
FIG. 6: a diagram schematically illustrating components of one of many embodiments of a consumer oriented system according to the disclosure.
Figure 7:
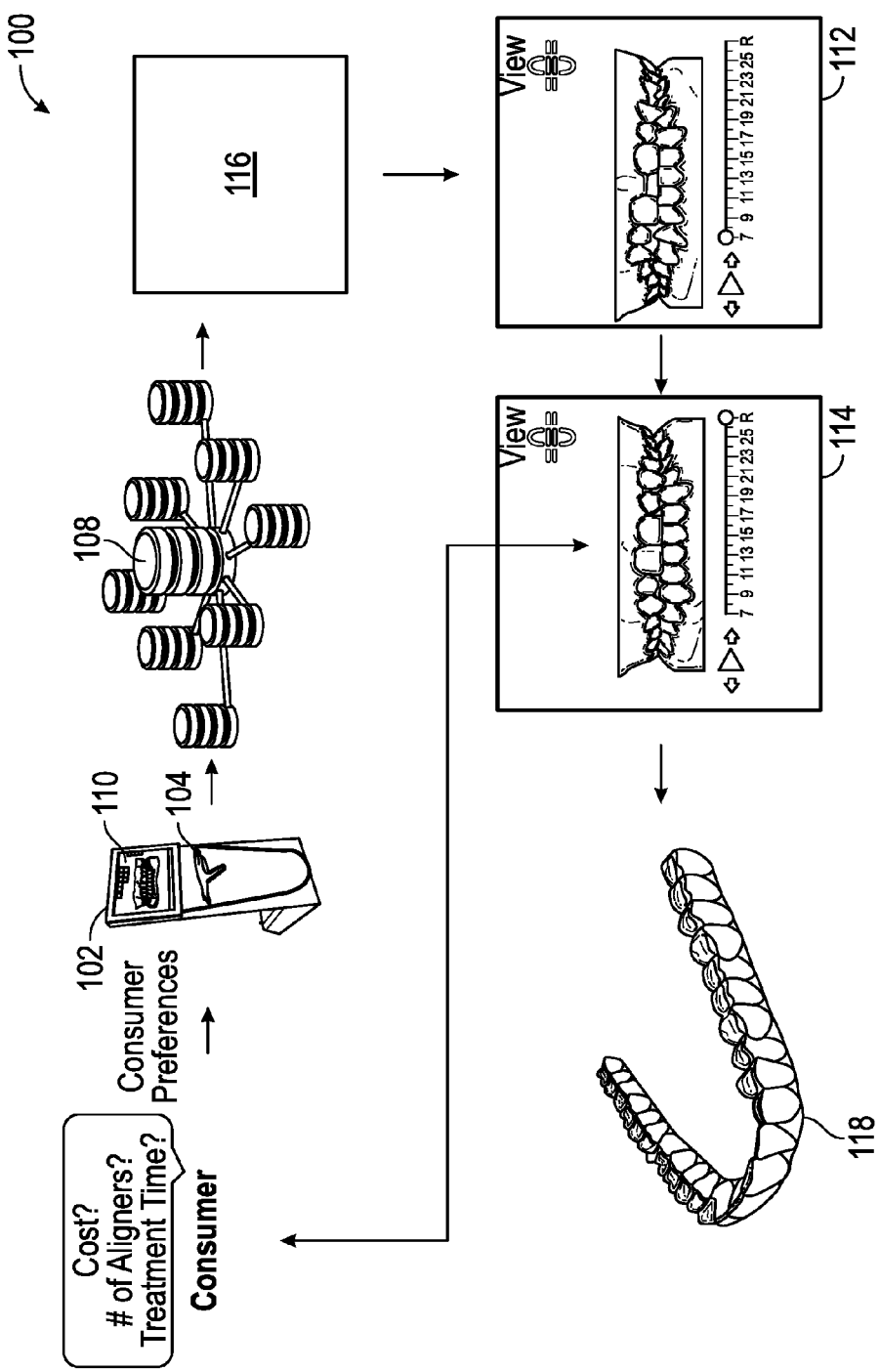
FIG. 7: a diagram schematically illustrating one of many embodiments of a method according to the system of FIG. 6.

With continuing reference to the figures, and particular reference to FIGS. 6-7, in at least one embodiment, a system or method according to the disclosure, which can be or include a system or method for diagnosing and/or identifying a treatment for an orthodontic condition, can include a system 100 for allowing or enabling a person, such as a patient or potential patient, to identify one or more variables or other data about his or her dental alignment or treatment of one or more dental conditions. For example, a system 100 can include a kiosk 102, such as a booth, stall, stand, or other structure, for allowing a consumer to take one or more steps for self-improvement of his or her dental alignment, which can include identifying such information as actual or potential treatment options, costs, number of appliances (e.g., aligners), treatment times, or other treatment-related data discussed in the present disclosure. In at least one embodiment, kiosk 102 can be adapted for use by a consumer without the assistance of a dental medical professional, such as in a location other than a dentist's office, which can be any location according to a need or application at hand, such as a retail store, mall, pharmacy, grocery store, or another location. In at least one embodiment, kiosk 102 can be or include a mobile or semi-mobile scanning station, such as a structure adapted to be moved from one retail location to another or placed within an existing retail location, or a user's mobile equipment, such as a camera, personal computer, smartphone (e.g., via a mobile application, or "app"), or other electronic device. In other words, system 100 can be said to depart from the traditional model of dental treatment (i.e., wherein a patient receives dental care directly from a dentist or other medical professional) in that system 100 can be adapted for allowing a patient to obtain at least one of a diagnosis and a treatment regarding a dental condition, whether separately or in combination with an opinion or care provided by a dentist, orthodontist, or other dental treatment professional.

In at least one embodiment, system 100 can include an imager 104 for capturing an image, model, or other representation of a patient's teeth, which can include recording information in one or more dimensions, such as 2D or 3D. Imager 104 can include any imaging equipment or other data input device desired for a particular application, such as one or more cameras (still or video), intra-oral scanners, x-ray machines, laser scanners, ultrasound scanners, or other imagers, such as magnetic resonance, low-dose x-ray, infrared, near infrared, or other imaging systems, whether separately or in combination. System 100 can include a processor 106, such as a computer, for processing data in connection with a patient's use of the system, a database 108, such as local or remote data storage media, for storing data in connection with a patient's use of the system and/or in connection with prior patient treatments, and a graphical user interface 110, such as a screen, touch screen or the like for displaying to, receiving input from, or otherwise interfacing with a user. System 100 can include any of the systems or components described elsewhere in this disclosure, and can involve performance of any of the methods described elsewhere in this disclosure, separately or in combination, in whole or in part. System 100 can include or employ any of the databases, servers, data, variables, approaches, or other items disclosed herein, including one or more of the algorithms or other manners of processing information, separately or in combination, in whole or in part, and in any number.

With continuing reference to the figures, one or more methods associated with system 100 and use of system 100 will be described. In at least one embodiment, a user, such as a patient or potential patient, can access system 100, such as via kiosk 102 (if present) or another user interface. A method can include imaging one or more of a user's teeth, such as with one or more imagers 104, which can, but need not include, imaging all of the user's teeth, for example in two or three dimensions. In at least one embodiment, a user or proxy can input one or more preferences, which can include any of the variables according to the present disclosure, such as, for example, which of one or more teeth to be aligned or otherwise treated, cost considerations, number of appliances, treatment time, rest periods (i.e., no active movement), retainer types, number of retainers, data regarding treatment history, or other information relating to a diagnosis or treatment for the user's teeth. Such inputs can be provided or requested at any time during use of system 100, separately or in combination, in whole or in part. In at least one embodiment, a user or proxy can provide feedback at one or more times during use of system 100, including for making changes to one or more preferences or parameters. A method can include generating one or more models of a set of teeth, which can include, for example, an initial model 112 and one or more subsequent models 114. In at least one embodiment, an initial model can represent a user's teeth at the time the model is generated, whether prior to any treatment or otherwise. Other models can include an actual or target representation of a user's teeth following a treatment or treatment regimen. A method can include generating any number of models according to an application of the invention, which can include an ideal model, whether ideal with regard to teeth generally or ideal with regard to a probable or other best case scenario for a given user.

In at least one embodiment, a method can include processing 116 one or more inputs, such as by way of one or more of the processes described herein, which can include accessing one or more servers or databases, and outputting one or more outputs. A method can include evaluating or otherwise processing an image or model 112, 114 of a user's teeth (and one or more other inputs, if present), computing a number, type, size, or configuration of aligners 118 to provide one or more corrections or other changes to the teeth, and displaying or otherwise outputting that information to a user, whether separately or in combination with one or more other outputs, such as cost, treatment options, or other data according to the present disclosure. In at least one embodiment, an output can include one or more models 112, 114 of a user's teeth, such as two- or -three dimensional representations of teeth following one or more treatments. In at least one embodiment, a method can include assigning a difficulty index to an orthodontic condition, evaluating an orthodontic condition or treatment for complexity, such as relative to one or more other orthodontic conditions or treatments, and determining a number of aligners for changing an orthodontic condition from one state to one or more other states, such as from a misaligned state to one or more relatively aligned states, which can, but need not, include an ideal orthodontic alignment. A method can include determining whether a need exists or may exist for one or more orthodontic treatments or devices other than aligners, whether separately or in combination with one or more aligners, such as for engagers, interproximal reduction, expansion, retainers, etc. A method can include determining and/or outputting one or more steps for treating an orthodontic condition, which can include identifying a type of aligner or other treatment device, a time or schedule for applying a device to a user's teeth, a time for reimaging of a user's teeth, such as to monitor progress of a treatment and/or reevaluate an ongoing treatment, or one or more other treatment parameters. A method can include responding to one or more user changes or other inputs, and providing one or more responses, which can, in at least one embodiment, be or include probabilistic responses, such as a percentage or other indications of a chance of success, number of prior and/or similar situations that have been treated or on which a diagnosis or treatment plan is based, statistics on time or times of treatment, or other information, such as numbers of appliances and costs. A method can include outputting one or more treatment plans based on type of treatment or aligner and one or more other inputs, and can include outputting two or more different treatment schedules or options, which, in at least one embodiment, can differ in one or more respects, such as with regard to stop/start times for active movement, treatment types, probable results, cost, or other variables.

Although illustrative embodiments of the present invention have been described herein, it should be understood that the invention is not limited to those described, and that various other changes or modifications may be made by one skilled in the art without departing from the scope or spirit of the invention.

What is claimed is:
1. A method for diagnosing and identifying a treatment for an orthodontic condition, comprising:
providing an intraoral imager configured to be operated by a patient;
receiving patient data regarding the orthodontic condition onto a server, the patient data comprising data from an intraoral image initiated by the patient;
accessing a database that comprises or has access to information derived from orthodontic treatments;
generating an electronic model of the orthodontic condition by defining at least two anatomic features of a set of teeth;
instructing at least one computer program to analyze the patient data and identify at least one diagnosis of the orthodontic condition based on the information derived from orthodontic treatments;
executing an algorithm based on one or more inputs derived from the information derived from orthodontic treatments;
instructing the at least one computer program to identify at least one treatment regimen for the at least one diagnosis, the at least one treatment regimen including at least one of a treatment approach, a corrective appliance and a combination thereof; and
outputting the at least one treatment regimen to the patient.

2. The method of claim 1, further comprising outputting to the patient at least one of a number of corrective appliances for the treatment regimen, a cost for the treatment regimen, a time for the treatment regimen, and a combination thereof.

3. The method of claim 1, wherein providing an intraoral imager configured to be operated by a patient comprises at least one of providing an intraoral imager, providing software configured for use with a patient's electronic device to produce an intraoral image, and a combination thereof.

4. The method of claim 1, further comprising providing a kiosk having a graphical user interface configured to receive input from and provide output to the patient.

5. The method of claim 1, further comprising computing at least one of a number, type, size and configuration of aligners for the patient's teeth, and outputting that information to the patient.

6. The method of claim 1, further comprising assigning a difficulty index to an orthodontic condition and determining a number of aligners for changing the orthodontic condition from a first state to a second state.

7. The method of claim 1, further comprising determining at least one rest period for the treatment regimen.

8. The method of claim 1, further comprising assigning a probability value to the at least one diagnosis, wherein the probability value represents a likelihood that the diagnosis is accurate.

9. The method of claim 1, further comprising assigning a probability value to the treatment regimen, wherein the probability value represents a likelihood the treatment regimen will change the orthodontic condition from a first state to a second state.

10. A system for diagnosing and identifying a treatment for an orthodontic condition, comprising:
a server configured to receive patient data;
a database that comprises or has access to information derived from orthodontic treatments;
an electronic model of the orthodontic condition that defines at least two anatomic features of a set of teeth;
at least one computer program housed within or accessible by the server and configured to:
analyze the patient data;
analyze the information derived from orthodontic treatments;
identify at least one diagnosis of the orthodontic condition;
execute an algorithm based on one or more inputs derived from the information derived from orthodontic treatments;
identify at least one treatment regimen for the at least one diagnosis, wherein the at least one treatment regimen includes at least one of a treatment approach, a corrective appliance and a combination thereof; and
an intraoral imager configured to be operated by a patient.

11. The system of claim 10, further comprising a kiosk, wherein the intraoral imager is coupled to the kiosk.

12. The system of claim 11, further comprising a graphical user interface, wherein the intraoral imager and the graphical user interface are configured to be used by the patient simultaneously.

13. The system of claim 10, wherein the intraoral imager comprises a mobile device having a camera.

14. The system of claim 10, further comprising wherein the at least one computer program is configured to assign a probability value to the at least one diagnosis, wherein the probability value represents a likelihood that the diagnosis is accurate.

15. The system of claim 10, further comprising wherein the at least one computer program is configured to assign a probability value to the treatment regimen, wherein the probability value represents a likelihood the treatment regimen will change the orthodontic condition from a first state to a second state.

16. A method for delivering a diagnosis and identification of a treatment for an orthodontic condition, comprising providing a graphical user interface that prompts a patient for electronic patient data regarding an orthodontic condition of the patient, the electronic data comprising data from an intraoral image initiated by the patient;
providing access, through the graphical user interface, to a database that comprises or has access to information derived from orthodontic treatments, the information derived from orthodontic treatments including an electronically stored data set for each patient treatment, wherein each data set includes data that represents at least one of (a) a location and position of one or more teeth subject of a corresponding patient treatment and (b) a previously diagnosed orthodontic condition for the corresponding patient treatment;
comparing coordinates that represent at least two anatomic features of a set of teeth to at least a portion of the information derived from orthodontic treatments accessible via the database;
identifying a best fit data set that represents a statistical or prioritized best fit for the coordinates;
identifying at least one diagnosis of the orthodontic condition by prioritizing at least a portion of the data from a plurality of the data sets; and
identifying at least one treatment regimen for the at least one diagnosis, the at least one treatment regimen including at least one of a treatment approach, a corrective appliance and a combination thereof; and
outputting the at least one treatment regimen to the patient.

17. The method of claim 16, further comprising outputting to the patient at least one of a number of corrective appliances for the treatment regimen, a cost for the treatment regimen, a time for the treatment regimen, and a combination thereof.

18. The method of claim 16, further comprising providing a kiosk comprising the graphical user interface and an intraoral imager configured to be used by the patient.

19. The method of claim 16, further comprising assigning a difficulty index to an orthodontic condition and determining a number of aligners for changing the orthodontic condition from a first state to a second state.

20. The system of claim 16, further comprising assigning a probability value to the at least one treatment regimen, wherein the probability value represents a likelihood the treatment regimen will change the orthodontic condition from a first state to a second state.

* * * * *